United States Patent [19]

Sorwick

[11] 4,330,874

[45] May 18, 1982

[54] MECHANICAL SECTOR SCANNER HEAD AND POWER TRAIN

[75] Inventor: Jack R. Sorwick, Parker, Colo.

[73] Assignee: Technicare Corporation, Solon, Ohio

[21] Appl. No.: 178,488

[22] Filed: Aug. 15, 1980

[51] Int. Cl.[3] .......................... G01S 15/02; A61B 5/02

[52] U.S. Cl. ...................................... 367/103; 73/620; 128/660; 367/151; 367/910

[58] Field of Search ............... 367/103, 104, 151, 910; 73/620, 629; 128/660, 661

[56] References Cited

U.S. PATENT DOCUMENTS

| | | | |
|---|---|---|---|
| 2,459,162 | 1/1949 | Hayes | 367/104 X |
| 4,084,582 | 4/1978 | Nigam | 73/620 X |
| 4,208,602 | 6/1980 | Stoller | 128/660 X |
| 4,274,421 | 6/1981 | Dory | 128/660 |

*Primary Examiner*—Richard A. Farley

*Attorney, Agent, or Firm*—Audley A. Ciamporcero, Jr.

[57] ABSTRACT

A curved faced, disc shaped transducer and an oppositely facing, circular angularly disposed mirror form the transmission and reception path of a mechanical sector scan imaging system. The transducer and mirror are mounted on a common axis, and a shaft upon which the mirror is affixed oscillates about that axis. Through a belt drive mechanism, a motor provides the oscillating motion, in turn scanning the ultrasound beams through the subject by virtue of the mirror motion. An optical encoder records positional information from the motor, for coordination of the mirror oscillation with transducer signals, and thereby for the assembly of a composite image.

6 Claims, 6 Drawing Figures

MECHANICAL SECTOR SCANNER HEAD AND POWER TRAIN

FIELD OF THE INVENTION

This invention relates to ultrasound imaging systems and methods, and more particularly to real time ultrasound imaging systems employing a sector scan rationale.

BACKGROUND OF THE INVENTION AND PRIOR ART

A concurrently filed, copending application of C. Hottinger, U.S. Ser. No. 178,482 entitled "ULTRASONIC IMAGING SYSTEM EMPLOYING REAL TIME MECHANICAL SECTOR SCANNER" and assigned to the assignee hereof, describes and claims a form of real time mechanical sector scanner wherein a positionally fixed, focusing transducer emits and receives ultrasound energy along an axis, and an oppositely facing sonic reflector or mirror is pivoted about a fulcrum on the axis, to reflect sonic energy between the transducer and the subject. Thus, beams between the reflection face and the subject lie in a different spatial plane than do beams between the transducer and the subject. In addition to setting forth the basic premise of such operation, the Hottinger application discloses respective embodiments wherein the mirror is located intermediate the transducer and the source of oscillatory motive power, and wherein the mirror is located "outboard" of the transducer relative to the source of oscillatory motive power. As stated in the Hottinger application, the former arrangement represents in essence the type of mechanical sector scanner as set forth in the instant application, and in relevant portion made the subject of the claims hereof.

It is an object of the present invention, given the basic design precepts entailed by the Hottinger application, to provide a relatively optimally designed sector scanner, especially suitable for abdominal soft tissue applications, but quite amenable to other applications as well, by locating the respective component parts in a mutually complimentary and overall more efficient arrangement.

It is a further object of the present invention to provide such designs which minimize load inertial forces attendant to oscillating mirrors, the number of rotary seals required to maintain the integrity of the fluid borne by the transducer head, and the overall mechanical complexity and structural bulk of the head.

It is a further object of the present invention to provide a stationary transducer, axially rotating mirror configuration wherein artifacts occasioned by mirror support systems are relatively minimized.

SUMMARY OF THE INVENTION

The present invention is grounded on the principle of placement of an axially oscillating sonic mirror physically close to the driving mechanism therefor, and placement of a fixed ultrasound transducer at the outboard end of the scanner head. Such placement is facilitated by utilization of a curved transducer face and an angularly oriented oscillating mirror closely facing the transducer, whereby a short, compact head results, which avoids undue or excessive spacing of the emergent ultrasound beam from the outside end of the scan head.

In a preferred embodiment, a compact housing has a chamber therein, filled with sonically conductive fluid, and carrying a positionally fixed ultrasound transducer at an outward extremity. Opposite the mirror, a rotatable shaft penetrates the chamber, and carries thereon a coaxial circular mirror which is angularly disposed to the axis, and which is rotatable on the axis. Hence, ultrasound energy between the transducer and the subject is reflected by the mirror, and the angular orientation of the beams in the body of the subject is determined by the position of the mirror. A motor, preferably a servo controlled three phase motor, is belt coupled to the mirror shaft, and oscillates the mirror back and forth through a predetermined angle. Periodically during the oscillation, and much more rapidly than the oscillation rate, the transducer is fired and a series of echoes is detected. As the mirror is so oscillated, a positional encoding mechanism, preferably an optical encoding wheel attached to the motor, records positional information for coordination of respective ultrasound beams to and from the transducer, and for consequent assembly of a composite sector image.

BEST MODE FOR CARRYING OUT THE INVENTION

Figure 1A:
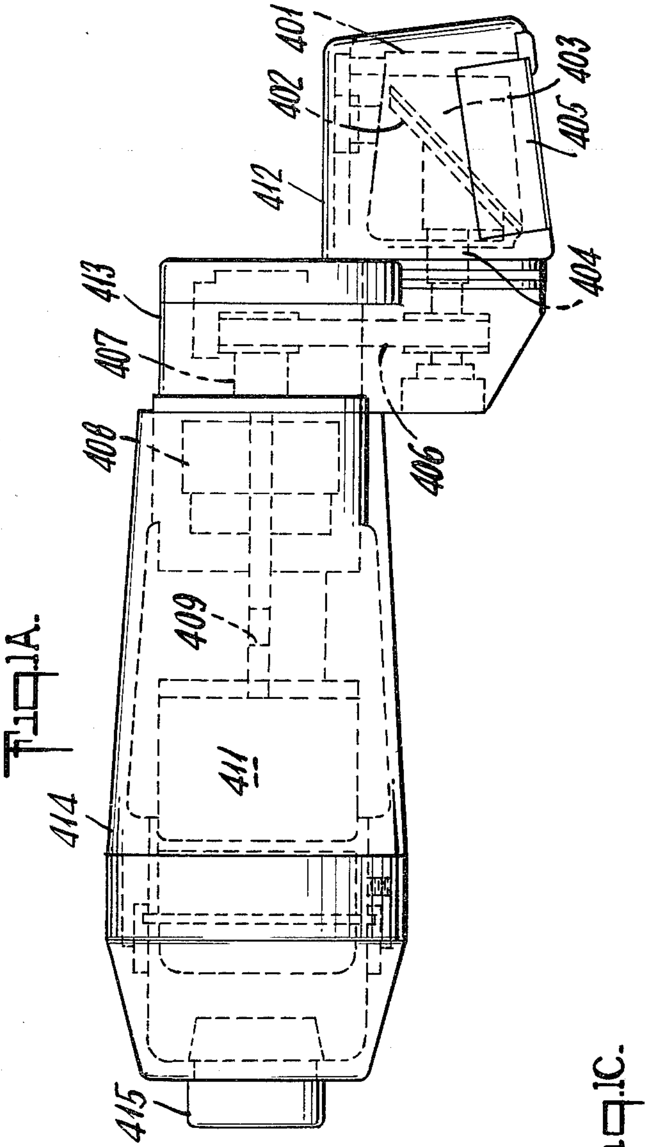
FIGS. 1A through 1C show respective cutaway views of a scan head, including motor and encoder, embodying the principles of the present invention.
Figure 1B:
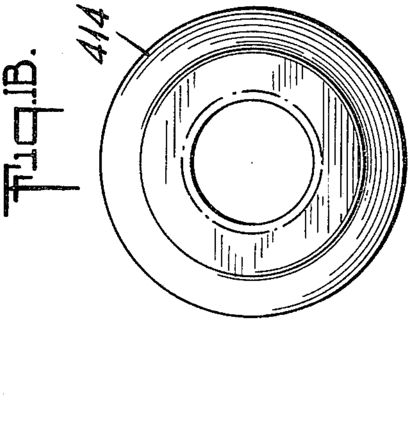
Figure 1C:
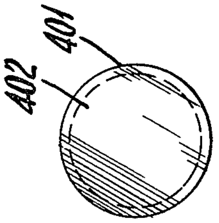

Referring first to FIGS. 1A through 1C, there is shown a preferred form of the principles of the present invention. That is, FIGS. 1A through 1C, and most especially the side view of FIG. 1A, show a complete mechanical sector scanner head, employing the basic transducer/mirror scheme described and claimed in the previously referenced Hottinger application, but, in accordance with the principles of the present invention, employing an advantageous, and for many applications, superior physical structure. FIG. 1A shows internal components in phantom, clearly designating the positioning of those components within a convenient and easily manipulated external housing. Moreover, it will be appreciated from the following description that the relative physical and functional correspondence of transducer, mirror, power sources, and encoders yields an overall efficient, and reliable configuration which substantially achieves the previously recited objects of the present invention.

Considering first the cross-section of FIG. 1A, it will be noted that the chamber 403 bearing the transducer and mirror, is located in a lowermost, outwardly disposed section 412 of the unit, and that the motor and encoder (i.e., the drive means) is located in an upper section 414. An intermediate section 413 interconnects upper section 414 with lower section 412, and provides for a transfer of power therebetween through the mechanism of a belt and pulley system. Two elastic diaphragms (not shown in FIG. 1) occupy the lower section 412 for purposes of providing expansion space for the liquid within the chamber 403 to accommodate the liquid volume increase accompanying increases in liquid temperature above ambient. A suitable grommet 415 provides a connection point for cables and the like whereby power, signal transmission and receipt, and the like are coupled to suitable imaging apparatus, as is known in the art. It is contemplated that the upper portion 414 defines a handle portion, which may be held by the user conveniently in one hand, while the lower portion 412, and most particularly a sonic window 405, is disposed against the body of the patient, with sonic energy being passed into, and received from the patient's body through the sonic window 405.

An axially rotatable mirror 402 is disposed just above the sonic window 405, the mirror being rotatable, preferentially in an oscillatory fashion, on a shaft 404 which penetrates the chamber 403 and which receives motive power by a drive belt and pulley system 406. A transducer 401 faces the mirror 402, to emit ultrasound energy towards the mirror, which in turn is deflected into the patient through window 405, and to receive ultrasound echoes which enter the chamber 403 through window 405, and are deflected by mirror 402 back to the transducer 401. It will be appreciated from FIG. 1A that the transducer 401, in accordance with the principles of the present invention, is located "outboard" of the mirror 402 relative to the source of motive power for the oscillation of the mirror 402.

The belt and pulley drive system 406 will be seen to exchange power between an upper shaft 407, emergent from a motor drive source 408, and the lower shaft 404 upon which the mirror 402 is carried. The shaft 409 continues outward from the motor 408 on the side opposite shaft portion 407, and into an encoder 411 which furnishes positional information concerning the shaft 409, and in turn the shaft 407, the belt and pulley system 406, the shaft 404, and ultimately the mirror 402. Thus, as the motor 408 provides oscillatory or rotational drive to the shaft 407, and in turn corresponding motion to the mirror 402, encoder 411 continuously records positional information thereof, whereby the imaging system is able to coordinate the position of mirror 402 with ultrasound signals which are emitted by transducer 401, and a corresponding echo signal train which is received by transducer 401.

As is described in greater detail in the previously mentioned Hottinger patent application, the transmission and receipt of signals from transducer 401 occurs at a frequency far greater than the rate of motion of the mirror 402, such that the motion of mirror 402 through a predetermined sector (e.g., 90°) is effectively divided into increments, each increment corresponding to a firing of the transducer 401, and the substantially immediate receipt of a pulse echo train from the patient via the mirror 402. The aggregate of these respective pulse-echo combinations, through the sector of mirror motion, is the production of an image of the patient's body tissue through a corresponding sector.

FIG. 1C shows a cutaway side view of the lower portion 412 of the FIG. 1A apparatus, merely illustrating the circular form and relative sizes of transducer 401 and mirror 402, in accordance with the principles of the present invention. The focusing character of the transducer 401, as described hereinafter, directs sonic energy onto the mirror 402, which as noted in cross-section in FIG. 1A, is disposed at a predetermined angle, preferably 45°, to the outboard transducer 401. FIG. 1B merely shows an end view of the upper portion 414 of the FIG. 1A embodiment, demonstrating the cylindrical character thereof, and the consequent convenient form for manipulation or handling by the user thereof.

Figure 2:
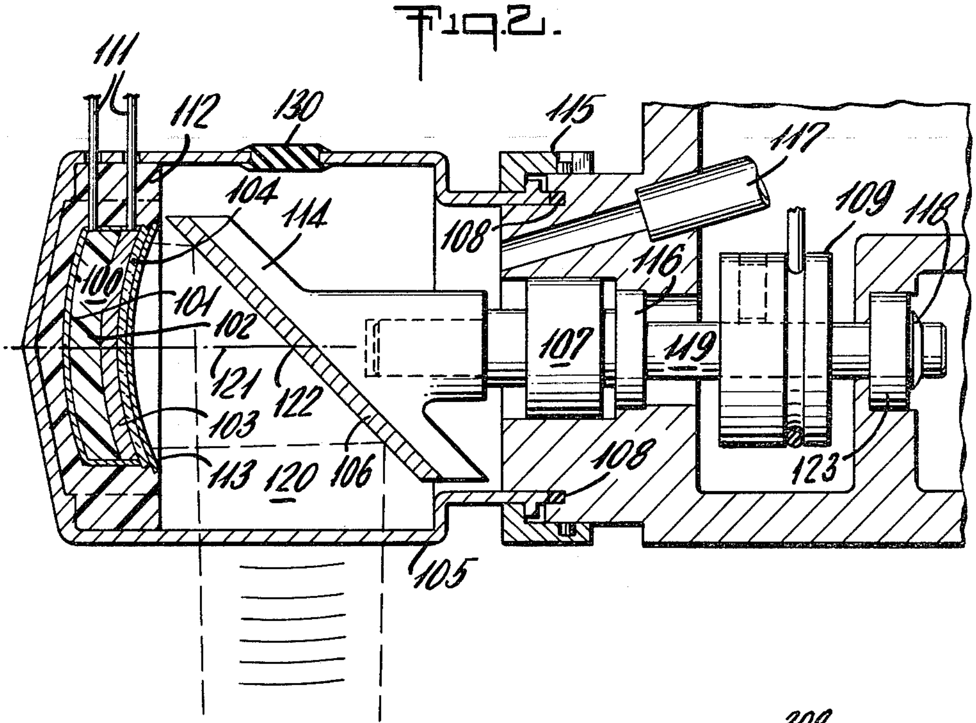
FIG. 2 shows a cross sectional detailed view of a mechanical sector scanner head embodying the principles of the present invention.

Referring to FIG. 2, there is shown the head portion of a mechanical sector scanner embodying the principles of the present invention. A housing 105 defines therein a chamber 120, which carries a sonically conductive fluid, such as water. As is known in the art, fluid within the chamber 120 may be provided with additives, such as alcohol, polymer based lubricant, or the like which tend to match the fluid to the sonic impedance of the body. The viscosity of the fluid is not critical, but for specific applications it may be useful to increase the viscosity of the fluid for purposes of damping spurious reverberation through the instrument.

A pair of leads 111 are connected to a round ultrasound transducer 100, constructed as is known in the art, for example, by successive layers of absorber backing 102, piezoelectric crystal 103, and matching layers such as 104 of vacuum deposited glass, and 113 an epoxy front piece. As shown, the transducer 100 is enclosed on the outboard side by an rf shield material 101, and is potted in a positionally fixed location in housing 105, such as by commercially available potting materials. As is also evident from the cross-sectional view of FIG. 1, the transducer 100 employs a curved (i.e., convex) front surface, whereby sonic energy generated as a consequence of electrical stimulation of the leads 111, comprises a focused travelling sonic wave, the focal characteristics of which will be dependent upon the desired depth of the image plane within the subject. That is, sonic energy from the transducer 100 is reflected by a sonic mirror 106, and thereby is folded downwardly toward the patient,and due to the focal characteristics of the transducer 100, the waves converge properly after exiting from the housing 105 as though the transducer was located directly thereabove. The transducer 100 is circular in configuration and is centered on an axis 121, about which sonic wavefronts emitted by the transducer are likewise centered, and along which the sonic energy moves. The rotation of the mirror 106 on axis 121, with transducer being stationary thereon, may be regarded as "relative torsional displacement".

As elastic diaphragm 130 allows for liquid thermal expansion and contraction, as previously discussed. It will be understood that several such diaphragms may be employed, and located pursuant to the desires of the designer.

The mirror mount upon which the sonic reflector 106 is affixed may be a cantilevered bracket having a streamlined figuration so that upon oscillation of the reflector, minimal turbulence of the surrounding fluid is encountered.

The chamber 120 also carries a sonic reflector means, basically including a low density mirror amount 114 onto which is fastened a sonic reflector 106, such as a disc of polished aluminum of glass. The mirror 106 is circular in configuration and as shown is maintained at a predetermined angle (e.g., 45°) to the axis 121. Hence, as shown in phantom, sonic energy from the transducer is deflected by the mirror 106 downwardly through the chamber 120, out through sonically transparent section of the housing 105, and thereupon into the patient. Similarly, sonic echoes from the patient return to the chamber 120, and are deflected by the mirror back to the transducer, there to be converted to electrical signals on leads 111.

In FIG. 2, the mirror 106 and mirror mount 114 are carried on a coaxial shaft 119. A bayonet type locking mechanism 115, sealing O ring 108, and a dynamic seal 107 maintain fluid in the chamber 120. A port 117 allows for introduction or withdrawal of fluid from the chamber 120. Bearings 116 and 123, with retainer 118, allow for rotation or oscillation of the shaft 119 on the axis 121, and in turn the axial displacement of the mirror 106 relative to the fixed transducer. Such motion is accomplished via a drive pulley 109, which is affixed to the shaft 119, and motor drive apparatus, not shown in FIG. 2.

In the FIG. 2 embodiment, central point 122 of mirror 106, which is located on axis 121 and in that sense renders the mirror 106 coaxial with the shaft 119 and with the transducer 100, essentially serves as a fulcrum for the motion of the mirror 106. It will be appreciated that, as the shaft 119 is rotated or oscillated through the application of motive force at the drive pulley 109, the mirror 106 correspondingly is moved. One may visualize a normal vector to the mirror 106 at the fulcrum point 122, which normal vector moves back and forth through a plane which intersects with the plane of wavefronts emerging from the transducer 100. As such normal vector moves, so also does the downwardly reflected ultrasound beam move, producing a scanning effect in the body of the patient.

Figure 3A:
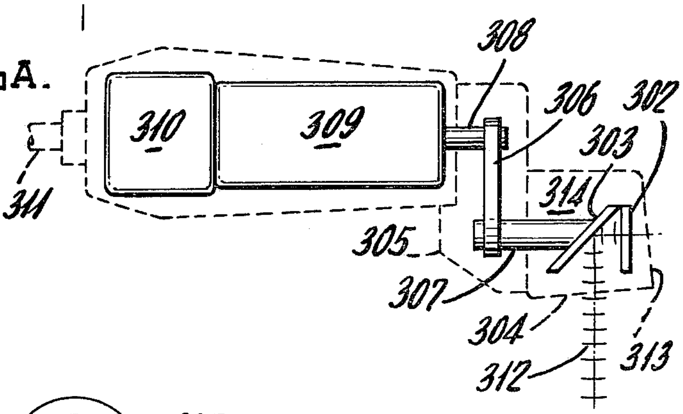
FIGS. 3A and 3B show operation of a preferred form of the principles of the present invention.
Figure 3B:
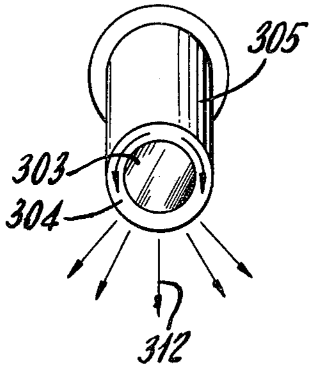

Consideration of FIGS. 3A and 3B will facilitate appreciation of the utilization of the embodiments of FIG. 1A or FIG. 2 in a scanning head which may be conveniently manipulated by the ultrasonographer.

Referring to FIGS. 3A and 3B jointly, the transducer 302 is positionally fixed within a lower portion 313 of the head, which forms the fluid chamber 314 and which carries therein the movable mirror 303. Mirror 303 is carried on a shaft 307, which is interconnected with a laterally displaced shaft 308 by means of a drive belt 306. A motor 309 either oscillates shaft 308 back and forth, or rotates it, as preferred, and correspondingly brings about similar movement of the mirror 303. For any given position of the mirror 303, there occurs a sonic wavefront from transducer 302, which is deflected by mirror 303 downwardly through sonic window 304 and, as shown symbolically at 312, into the body of the patient. Substantially instantaneously compared to the rate of motion of the mirror 303, an echo signal train returns to the transducer 302 via the mirror 303. As noted in FIG. 3B, the aggregate of these separate events, resulting from the motion of mirror 303 through a predetermined sector, is the assembly of a sector shaped image of the rotational plane in the body.

Since the mirror 303 moves under the power of the motor 309, it will be appreciated that the motion of the mirror needs to be coordinated with the transducer operation, i.e., with the transmission of sonic energy into the body, and receipt of echoes from the body. Accordingly, an encoder 310 is shown next adjacent the motor 309, which encoder 310 serves the function of positionally encoding the motion of motor 309 and in turn of mirror 303. Such positional information is important for production of an image display, by interrelating signals to and from the transducer 302.

It will be appreciated that numerous commercially available and well-known motor and encoder schemes will be suitable for utilization in accordance with the principles of the present invention. For example, the motor 309 may properly be embodied either as a continuous (e.g., three phase) motor or as a stepping or incremental motor. Likewise, the encoder 310 may be embodied by a Hall effect switch, or a continuous optical wheel type encoder system such as are commercially available. One such system is sold by Teledyne-Gurley of Troy, N.Y., under the trade designation Model 8602-69, Rotary Incremental Encoder.

It will be appreciated that the foregoing sets forth preferred and illustrative embodiments of the principles of the present invention, and that numerous alternatives may occur to those of ordinary skill in the art without departure from the spirit or the scope of the present invention.

I claim:

1. In an ultrasound imaging system, apparatus for developing a composite sector image along a given plane in the body of a subject comprising:

(a) a housing defining a chamber therein, having respective opposite ends on a given axis, and defining a side between said ends;

(b) a transducer affixed at one end of said chamber for generating and receiving sonic energy along said axis;

(c) shaft means, coaxial with said given axis, penetrating the end of said chamber opposite the transducer;

(d) a sonic reflector means, in said chamber attached to said shaft means, having a sonic reflection surface facing said transducer at a predetermined angle to said axis for deflecting sonic energy between said transducer and said side;

(e) a sonically transparent window on said side, adapted to engage the subject, for free passage of sonic energy between the subject and said reflector means;

(f) sonically conductive fluid filling said chamber;

(g) motive means, connected to said shaft, for oscillating movement of said reflector means; and (h) wherein said housing further includes:

(i) a first, outboard portion, carrying said chamber;

(ii) a second, inboard portion, carrying said motive means; and (iii) a third intermediate portion, carrying means for transfer of oscillatory motive force from said motive means in said second portion to said shaft in said first portion.

2. Apparatus as described in claim 1 wherein said motive means comprises a motor having an oscillating drive shaft, and encoder means for encoding the position of said shaft.

3. Apparatus as described in claim 2 wherein said motor and drive shaft are located on an axis which is substantially parallel to, but spaced a distance apart from said given axis.

4. Apparatus as described in claim 3 wherein said means for transfer comprises belt means between said drive shaft and said shaft means, whereby said motor oscillates said reflector means.

5. Apparatus as described in claim 1 wherein said sonic reflector surface is flat and disc shaped, and wherein said transducer is configured as a disc but defines a curved beam shaping and focusing surface facing said mirror.

6. Apparatus as described in claim 1 wherein said sonic reflector means comprises a cantilevered bracket attached to said shaft means, having a sonic mirror disc affixed thereto, said bracket having a streamlined configuration for minimal turbulence of said fluid as said reflector means oscillate.

* * * * *